United States Patent [19]

Sarin et al.

[11] Patent Number: 6,022,955
[45] Date of Patent: Feb. 8, 2000

[54] FATTY ACID — PULMONARY SURFACTANT CONJUGATES

[75] Inventors: Virender Kumar Sarin, Libertyville, Ill.; Darryl Robin Absolom, Columbus, Ohio; Shanker Lal Gupta, Vernon Hills, Ill.

[73] Assignee: Abbott Laboratories, Abbott Park, Ill.

[21] Appl. No.: 07/808,075

[22] Filed: Dec. 10, 1991

Related U.S. Application Data

[63] Continuation of application No. 07/525,581, May 21, 1990, abandoned.

[51] Int. Cl.[7] .............................. C07K 1/00; C07K 14/00; C07K 5/00; C07K 7/00
[52] U.S. Cl. .......................... 530/410; 530/350; 530/324; 514/12
[58] Field of Search .................................. 530/410, 350, 530/324; 514/12

[56] References Cited

U.S. PATENT DOCUMENTS

| | | | |
|---|---|---|---|
| 4,234,475 | 11/1980 | Sokol | 530/357 |
| 4,406,833 | 9/1983 | Boehme et al. | 530/410 |
| 4,659,805 | 4/1987 | Schilling, Jr. et al. | 580/350 |
| 4,861,756 | 8/1989 | Jackson | 514/11 |
| 4,882,422 | 11/1989 | Taeusch | 530/350 |
| 4,918,161 | 4/1990 | Steinbrink et al. | 530/300 |
| 4,933,280 | 6/1990 | Schilling, Jr. et al. | 435/69.1 |
| 5,013,720 | 5/1991 | Whitsett | 514/12 |

FOREIGN PATENT DOCUMENTS

WO87/06943  11/1987  WIPO .................. 530/324

OTHER PUBLICATIONS

Curstedt, T. et al., *Proc. Natl. Acad. Sci.*(USA), vol. 87: 2985–2989, Apr. 1990.
Smith, G., et al., *Pediatric Research*, vol. 23(5): 484–490, 1988.
Curstedt, T. et al., *Eur. J. Biochem.*, 168: 255–262, 1987.

*Primary Examiner*—Avis M. Davenport
*Attorney, Agent, or Firm*—Thomas D. Brainard; J. Michael Dixon

[57] ABSTRACT

This invention discloses a method for chemically modifying a pulmonary surfactant protein or polypeptides with various fatty acids. These conjugates are useful in preparing formulations for the treatment of respiratory disease.

16 Claims, No Drawings

FATTY ACID — PULMONARY SURFACTANT CONJUGATES

This is a Continuation of application Ser. No: 07/525,581, filed May 21, 1990 now abandoned.

TECHNICAL FIELD

This invention relates to fatty acid polypeptide conjugates and the use of these conjugates in the preparation of novel formulations for the treatment of respiratory disease.

BACKGROUND OF THE INVENTION

The present invention relates to novel compositions of matter and methods for the treatment of respiratory distress with these novel compositions. This invention also relates to the chemical modification of the polypeptides or protein fragments which enhance the surfactant-like properties of phospholipids. More specifically, the present invention relates to the covalent attachment of fatty acids of various chain lengths to polypeptides comprising fragment replicas and analogs of fragment replicas of the naturally occurring low molecular weight hydrophobic surfactant associated proteins known as SP-B and SP-C and to their use in the formulation of novel medicaments useful in the establishment, modification and/or maintenance of pulmonary surface tension.

Specifically incorporated herein, by reference for purposes of establishing the background of the present invention, are the teachings and disclosures of the following U.S. Patent Applications:

1. U.S. patent application Ser. No. 860,239, filed May 6, 1986;
2. U.S. patent application Ser. No. 060,719, filed Jun. 10, 1987;
3. U.S. patent application Ser. No. 101,680, filed Oct. 1, 1987;
4. U.S. patent application Ser. No. 397,151 filed Aug. 22, 1989.

Also incorporated herein by reference are U.S. Pat. No. 4,659,805 and U.S. Pat. No. 4,882,422 which disclose and claim a high molecular weight surfactant protein known as SP-A. Also incorporated herein by reference is U.S. Pat. No. 4,918,161 which discloses and claims a low molecular weight surfactant protein known as SP-B.

In general, these references disclose the discovery, method of isolation, characterization and use of a family of naturally occurring mammalian surfactant-associated proteins. Members of this family have been designated as SP-A, SP-B and SP-C. These proteins are known to have the capacity to effect the surfactant-like activity of both natural and synthetic phospholipids. It should be noted that the associated scientific literature also uses the nomenclature of SAP-B, SAP-(Phe), SAP-6 (Phe), and SPL-(Phe) for SP-B. SP-C is also referred to as SAP-C, SAP-(Val), SAP-6 (Val) and SPL (Val) in the prior art. These two proteins (SP-B and SP-C) are distinct gene products with unique amino acid sequences. Both proteins are derived from proteolytic processing of larger precursor proteins synthesized by pulmonary type II epithelial cells.

SP-B is generated by cleavage of the precursor protein at a glutamine-phenylalanine peptide bond resulting in the naturally occurring protein having 78 amino acid residues, with an N-terminal residue of phenylalanine and a simple molecular weight of about 8,700. SP-B isolated from human lung migrates on polyacrylamide gels as an entity having a relative molecular weight ($M_r$) of 7–8,000 after sulfhydryl reduction. Without sulfhydryl reduction the naturally occurring protein is found as large oligiomers. SP-B is extremely hydrophobic, a physical property which is consistent with its in vivo strong association with phospholipids and solubility in organic solvents such as chloroform and methanol.

SP-C has an amino terminal glycine or phenylalanine residue, a molecular weight of about 3,700, a polyvaline sequence, and, like SP-B, is also extremely hydrophobic. In addition, both proteins (SP-B and SP-C) are substantially resistant to enzyme degradation by proteases such as trypsin, chymotrypsin, staphylococcus nuclease V-8, endoglycosidase F, and collegenase. Neither SP-B nor SP-C exhibits any degradation or alteration in their molecular weight distribution following treatment with these enzymes. In this behavior, as well as on the basis of amino acid sequence information, the proteins are clearly different from the more hydrophilic and higher molecular weight protein SP-A (also known as SAP-35).

SP-A is present in natural lung surfactant material and has a reduced molecular weight of 30–36,000. SP-A is a glycoprotein containing an internal collagen-like region which is rich in glycine and hydroxyproline. This protein has a N-linked complex carbohydrate and a calcium binding site in the C-terminal globular domain. SP-A is known to bind to phospholipids and is thought to confer important structural organization to the surfactant lipids. This protein is also believed to play a role in preventing the inhibition of pulmonary surfactant activity by plasma or other proteins.

The complete amino acid sequence of SP-B and SP-C has been determined from amino acid analysis and deduced from DNA's derived from the mRNA's encoding the proteins. The SP-B and SP-C proteins are available as isolates from natural sources, such as bronchioalveolar lung washes and minced lung tissue or as products resulting from the application of recombinant DNA methodologies. When formulated with phospholipids (including synthetic phospholipids) these proteins provide compositions useful in the treatment of pulmonary disorders.

As is often the case with biologically active substances, the isolation of substantial quantities of hydrophobic SP-B and SP-C proteins from natural sources is expensive and labor intensive. Production of these proteins by recombinant DNA techniques requires substantial effort in terms of design and achieving optimal host/vector expression systems to facilitate production of the proteins. In addition, considerable effort is required to develop effective isolation strategies to separate and purify the expressed protein of interest from the unwanted material. Solid phase peptide synthesis is a feasible alternative for obtaining both SP-B and SP-C. However, in either production scenario the low molecular weight, extreme hydrophobicity and large number of valine residues markedly complicates commercial exploitation of the material.

The principal difficulty arises from the extreme hydrophobicity and hence markedly limited solubility of the SP-C polypeptide (regardless of its mode of production) resulting from its primary amino acid sequence and high valine content. As a consequence it is necessary to utilize chemically and clinically unacceptable solvents, (e.g. concentrated formic acid) to solubilize the polypeptide. Complete removal of such solvents is not only necessary in order to minimize oxidative damage to other components of the admixture, but is also difficult owing to the low vapor pressure of these solvents. As a consequence extremely time consuming and laborious strategies need to be developed.

The medical community has a need for commercial quantities of SP-C which can be readily utilized in pharmaceutical formulations (i.e. admixtures with phospholipids and the like). The present invention fulfills that need through the discovery that covalent attachment of various fatty acids (FA) to SP-C markedly improves the solubility of the FA-SP-C conjugates in solvents such as ethanol and/or methanol.

The usefulness of the naturally occurring SP-B and SP-C proteins resides in their ability to significantly improve the surface tension lowering capacity and respreadability of phospholipid admixtures. Natural SP-B and SP-C have been shown, both individually as well as in combination, to facilitate this improvement in surfactant-like activity of phospholipids. However, use of the unmodified SP-C sequence (i.e. no covalently attached fatty acid) results in admixtures preparations having variable surface properties. It is believed this is due to batch-to-batch variation in SP-C solubility.

The prior art fails to suggest, disclose or contemplate the instant discovery which is, in part, the conjugation of a fatty acid to SP-C. Further one skilled in the art can not a priori predict which fatty acids when covalently attached to SP-C will evidence utility or that certain FA-SP-C conjugates will have activity exceeding that of the complete unmodified natural protein or polypeptide.

It is thus clear that FA-SP-C conjugates or analogs thereof, would provide numerous advantages over the use of unmodified SP-C produced by chemical or recombinant synthesis. These advantages include ease and reproducibility of admixture formulation and significant cost savings resulting from the ability to utilize polar solvents. The FA-SP-C conjugates can be combined with phospholipids or with natural SP-B, or with recombinantly expressed SP-B, solid phase synthetic full length SP-B, or fragments and/or analogs thereof to produce useful formulations.

DISCLOSURE OF THE INVENTION

There is disclosed a composition of matter comprising a covalently linked compound consisting of two parts and having the structural formula FA-SP-C wherein -SP-C is a protein selected from the group comprising human, porcine, canine, bovine surfactant associated protein C (-SP-C) either naturally derived or produced by peptide synthesis or recombinant DNA means and wherein FA- is a fatty acid.

There is further disclosed a composition of matter comprising a compound having the structural formula FA-SP-C wherein SP-C is a protein selected from the group comprising human, porcine, canine, bovine surfactant associated protein C (-SP-C) either naturally derived or produced by peptide synthesis or recombinant DNA means and wherein -FA is a fatty acid selected from the group comprising fatty acids having a carbon chain length from two (2) to about twenty (20) carbon atoms.

This novel entity comprises a fatty acid (FA) covalently attached to the SP-C protein (or analogs thereof). These covalent SP-C adducts or conjugates (FA-SP-C) exhibit improved solubility and enhanced surfactant activity when admixed with phospholipids either alone or in combination with SP-B and/or fragments of SP-B. The SP-B fragment being that portion of the SP-B protein which contains at least the terminal amino acid sequence and substitution, deletion and addition analogs thereof.

There is also disclosed a composition of matter comprising a fatty acid/SP-C conjugate (or analogs thereof) in combination with at least one lipid. The lipid is selected from the group consisting of synthetic phospholipids, naturally occurring phospholipids, neutral lipids, cholesterol, cholesterol esters, phosphatidylcholine, disaturated phosphatidylycholine, phosphatidylglycerol, dipalmitoyl phosphatidylcholine, phosphatidylihisotyl and mixtures thereof.

The most preferred lipids are a mixture comprising dipalmitoyl-sn-phosphatidylcholine (DPPC), egg phosphatidylglycerol (PG) and palmitic acid (PA).

Also disclosed is a method for the treatment of pulmonary surfactant deficient states (e.g. hyaline membrane disease) and/or abnormal surfactant states (e.g. respiratory distress syndrome), said method comprising the administration of an effective amount of a surfactant composition to a patient in need of treatment, said surfactant composition comprising a FA-SP-C conjugate and at least one lipid. The FA-SP-C conjugate may be employed alone or in combination with full length SP-B or a SP-B fragment, said fragment contains at least a terminal amino acid sequence; and at least one lipid.

Further disclosed is a method for pulmonary drug delivery, said method consisting of administering to a patient in need, a therapeutically effective amount of a composition comprising: 1) a FA-SP-C conjugate either alone or in combination with fragment of the SP-B protein that contains at least a terminal amino acid sequence; 2) at least one lipid; and 3) an appropriate therapeutic agent.

Also disclosed is a method for the preparation of polyclonal antibodies exhibiting specificity for the antigenic determinants on natural SP-C, said method comprising immunizing with an effective amount of a composition comprising the FA-SP-C conjugate with suitable carriers and/or adjuvants.

According to the present invention, novel, non-naturally occurring peptide-fatty acid conjugates are disclosed which demonstrate improved solubility in some organic solvents and which have the ability to markedly enhance the surfactant-like activity of natural and/or synthetic phospholipids. The novel chemical entities of this invention comprise the conjugates of fatty acids covalently attached to the known sequences of naturally occurring SP-C. This conjugate which may be combined with phospholipids alone, or combined with natural, synthetic or recombinant SP-B and/or SP-A, or combined with one or more SP-B fragments, said fragment being that portion of the SP-B protein which contains at least a terminal amino acid sequence and substitution, deletion, replicate and addition analogs thereof. The FA-SP-C conjugates of the invention are readily and economically produced via chemical means and may be formulated with natural and/or synthetic phospholipids.

The fatty acids useful in preparing the conjugates of this invention are the fatty acids of 2 to about 20 carbon atoms. The preferred FA-SP-C conjugates of the invention are:

C-14 (Myristic acid)-SP-C;

C-16 (Palmitic acid)-SP-C.

C-20 (Arachadic acid)-SP-C

The most preferred fatty acids useful in this invention are the fatty acids of 14–16 carbon atoms. Furthermore, it is also contemplated that the preferred fatty acids (of certain chain lengths, both saturated and unsaturated) may also include lipase resistant analogs such as the ether, phosphoryl, and/or sulfur derivatives of these fatty acids.

It is contemplated that the SP-C polypeptide useful in this invention may include addition analogs (wherein one or more amino acid-residues which are not naturally present in a given SP-C sequence are provided in the synthetic polypeptide at terminal or intermediate locations), deletion analogs (wherein one or more residues are deleted from a natural sequence), substitution analogs (wherein one or more residues are replaced by other amino acid or modified residues) and replicate analogs (wherein one or more residues are repeated, replicated, in a natural sequence). Specifically comtemplated are interspecies hybrid analogs comprising composite replicas of more than one species (i.e. human, canine, bovine, porcine, etc.) of naturally occurring SP-C proteins and those analogs wherein D-forms of amino acids replace the naturally occurring L-forms. The polypeptides useful in this invention preferably retain the overall hydrophobic character of the SP-C protein and are also expected to retain substantial elements of secondary and tertiary conformation.

Unlike unmodified SP-C (native, synthetic or recombinant) the FA-SP-C conjugates of this invention are readily formulated with either natural or synthetic phospholipids to yield admixtures which are useful in the treatment of pulmonary surfactant deficient (eg. hyaline membrane disease) and/or abnormal (eg. respiratory distress syndrome, RDS) surfactant states, and for pulmonary drug delivery systems. The FA-SP-C conjugates of this invention are also expected to have considerable use in the preparation of polyclonal and monoclonal antibodies exhibiting specificity for the antigenic determinants occurring on natural SP-C and which would therefore be useful inter alia in immunopurification and/or quantitative assessment of the SP-C protein in clinical immunodiagnosis.

Other aspects and advantages of the invention will be apparent upon consideration of the following detailed description of the invention and are intended to be illustrative embodiments thereof and not limitative.

Best Mode for Carrying Out the Invention

A number of fatty acids of varying chain length were covalently attached to SP-C synthesized by means of solid phase peptide synthesis. However, identical and/or similar SP-C could also be produced by known recombinant methodologies and the like.

The fatty acids of various chain lengths ($C_2$ to $C_{20}$) were covalently attached to the N-terminal end of SP-C by means of an symmetric anhydride reaction which is well known in the art. The fatty acids may be saturated or unsaturated entities. It will be readily appreciated by one skilled in the art of organic and/or protein chemistry that several alternative coupling strategies could be employed to achieve the same result. Furthermore, the fatty acids could also be attached to alternative sites on the SP-C molecule, e.g. the carboxyl terminal, ε-amino terminal group of lysine residues, SH groups of cysteine, etc. Fatty acid chain lengths greater than two (2) carbon atoms were found to yield enhanced solubility of the corresponding FA-SP-C conjugates and improved surfactant activity of the resultant FA-SP-C/phospholipid admixtures.

Thus, the scope of the present invention includes all SP-C regardless of origin and all chemical methods available for coupling saturated or unsaturated fatty acids to the SP-C polypeptide. The resulting FA-SP-C conjugates when combined with phospholipids exhibit enhanced surfactant activity as compared to unmodified SP-C. These conjugates can be facilely produced by relatively standard organic chemistry techniques.

As a result of formulation experiments and biophysical testing thereof (as hereinafter described) the inventors have determined that certain of these FA-SP-C conjugates exhibit an unexpected, unpredicted, unusual and surprising ability to facilitate enhanced surface activity of the resultant phospholipid admixtures.

Experimental

The following examples relate to the synthesis and testing of of FA-SP-C conjugates of the invention. More specifically, Example 1 and 2 relate to the organic synthesis and solubility testing of the various fatty acid chain length SP-C conjugates. Table 1 sets forth the nomenclature, fatty acid chain length and solubility of the various synthesized FA-SP-C conjugates. This data indicates that covalent attachment of fatty acids to SP-C results in markedly improved solubility as compared to the unmodified SP-C.

Examples 3 to 5 relate to the formulation and testing of various FA-SP-C/phospholipid admixtures. Tables 2 and 3 summarize the dynamic surface tension and adsorption data obtained with the various peptide-lipid admixtures using the modified Wilhelmy surface balance and pulsating bubble apparatus, respectively. The data illustrate markedly improved surfactant-like activity of the carrier phospholipids when combined with the conjugates of this invention.

As mentioned previously the SP-C used in this evaluation was prepared by solid phase synthesis but may also be prepared by recombinant DNA technology or any known technology. The fatty acids employed may be saturated, unsaturated or polyunsaturated whilst the covalent coupling may be achieved by any of known methods.

EXAMPLE 1

Synthesis of Fatty Acid Conjugated SP-C (1–34)

A molecule was made so as to provide a replica of the entire 34 amino acid residue sequence of the native human SP-C protein said sequence consisting of the sequence defined by the standard single letter amino acid code G-I-P-C-C-P-V-H-L-K-R-L-L-I-V-V-V-V-V-V-L-I-V-V-V-I-V-G-A-L-L-M-G-L.

This polypeptide was assembled on a phenylacetamidomethyl (PAM) resin support by stepwise solid phase synthesis (starting with the carboxyl terminal residue) according to the general procedure described by Barany, G. & Merrifield, R., in *The Peptides*, Gross, E. and Meienenhofer, J. Eds, 2 1–284, Academic Press, New York, N.Y., 1980. The C-terminal amino acid residue, leucine (Leu) was coupled to the PAM resin support via an oxymethyl phenylacetamidomethyl (OMPA) linkage, owing to the enhanced acid stability of the PAM resin which thereby ensures improved stability during prolonged treatment with trifluoroacetic acid (TFA). Following C-terminal (Leu) coupling, the resin (0.76 m mole/g, 0.66 g) was transferred to the reaction vessel of an Applied Biosystems Peptide Synthesizer model 430A. The next 13 amino acids were coupled in a stepwise manner using a preformed symmetric anhydride coupling protocol. The synthesis was then continued using the double coupling protocol for all subsequent amino acids. All amino terminal residues were protected by t-butyloxy carbonyl (t-Boc) linkage. In the first coupling, protected amino acids, except for histidine and arginine, were coupled using preformed symmetric anhydrides dissolved in DMF. The symmetric anhydride of an individual amino acid was formed in methylene chloride followed by solvent exchange to DMF before transferring to the reaction vessel of the peptide synthesizer. The second coupling of symmetric anhydride was conducted in methylene chloride. The amino acids arginine and histidine were coupled using the DCC/HOBT protocol. After incorporation of methionine at position 32, ethanedithiol (0.25%)(v/v) was added to TFA. This modified solution was employed for subsequent removals of the $N^\alpha$ BOC protecting groups up to proline at position 6. After incorporation of proline (position 6), TFA in $CH_2Cl_2$ was used according to the manufacturer's protocol.

The functional side chains of various amino acid residues were protected by the following groups:

| | |
|---|---|
| Arg-Tos | (Tosyl) |
| Lys-2ClZ | (2-Chlorobenzlyoxycarbonyl) |
| His-Tos | (Tosyl) |

The amino acid methionine was used without any side chain protection.

A small amount of peptide-resin (0.2 g) was removed after coupling of leucine at position 21. The integrity of the assembled peptide sequence on the resin support was verified by solid phase sequencing of the peptide fragment, and at the completion of the synthesis on an ABI 470A gas phase sequencer. After incorporation of glycine at position 1, approximately half of the swollen peptide-resin in methylene chloride was transferred to a manual reaction vessel. The $N^\alpha$-BOC group was removed, peptide-resin neutralized, and washed according to the standard protocol; then reacted with preformed symmetric anhydride of palmitic acid for five hours at room temperature. Preformed symmetric anhydride of palmitic acid (C16) was generated as follows:
  i) Dissolve 2 mmol of palmitic acid in a mixture of methylene chloride (3 ml) and chloroform (1 ml). Add 2 ml of 0.5M dicyclohexylcarbodiimide solution in $CH_2Cl_2$;
  ii) Stir the reaction mixture at room temperature for 10–15 minutes; and
  iii) White precipitates formed were filtered and the filtrate transferred to the manual reaction vessel containing peptide-resin.

At the completion of the first coupling cycle, the peptide-resin was washed three times with $CH_2Cl_2$ for one minute each, once with 5% diisopropylethylamine in $CH_2Cl_2$ for two minutes followed by three washes of $CH_2Cl_2$ for one minute each. Palmitic acid was then recoupled using 1 mmol of preformed symmetric anhydride for 20 hours at room temperature. It was then washed extensively with $CH_2Cl_2$ and a small amount (7.5 mg) of the resin was subjected to ninhydrin reaction for monitoring the unreacted amino groups.

The fully protected peptide-resin (390 mg) was allowed to swell in methylene chloride for five minutes. The swollen peptide-resin was then treated with approximately 10 mL of anhydrous hydrogen fluoride (HF) to which 1 ml p-cresol, 0.2 g p-thiocresol and 1 ml of dimethylsulfide (DMS) had been added for 60 minutes at 0° C. This results in the cleavage of the protein or peptide from the resin.

The HF/DMS was distilled off in vacuo at 0° C. The cleaved peptide and resin were washed three times with 15 mL aliquots of cold diethyl ether, and the free peptide was then extracted by washing: 1) three times with 10 ml washes of methanol ($CH_3OH$); 2) three times with 10 mL of chloroform ($CHCl_3$); and 3) three times with 10 mL of $CHCl_3$: $CH_3OH$ (1:1, v/v). All the extracts were combined and then evaporated to dryness to yield a white solid which was dried overnight under vacuum to yield approximately 160 mg of the peptide. The remaining peptide-resin was then extracted twice with 6 mL each of cold TFA. The wash was immediately filtered, and the FA-SP-C conjugate precipitated by the addition of 50–60 ml ice-cold water. The crude FA-SP-C peptide was then collected as a pelleted solid by centrifugation. The pellet was washed with 15 ml of diethyl ether and then centrifuged. This wash procedure was repeated three times with diethyl ether.

The amino acid composition of the conjugate was determined by acid hydrolysis (12N HCl/TFA; 2:1, v/v) containing 5% (v/v) thioglycolic acid at 150° C. for four hours in vacuo. After removal of the acid, the hydrolysate was analyzed on a Beckman 6300 amino acid analyzer. It was also analyzed by plasma desorption mass spectroscopy. The conjugate was dissolved in n-propanol and a UV spectrum from 210 nm to 330 nm on a Beckman DB Spectrophotometer was also obtained. The observed spectra from both techniques were as expected for the fatty acid conjugate.

Other fatty acid conjugated SP-C peptides were synthesized in a manner similar to that described above. The fatty acids utilized include the following carbon chain lengths:

| | |
|---|---|
| C2, | (Acetic) |
| C14 | (Myristic) |
| C16 | (Palmitic) |
| C18 | (Stearic) |
| C20 | (Arachidic) |

It is clear from the data contained in Table 1 that covalent attachment of fatty acids of a carbon chain length greater than two (2) carbon atoms results in a marked improvement in solubility of the FA-SP-C conjugate as compared to unmodified SP-C.

EXAMPLE 2
Solubility of Various Fatty Acid-SP-C Conjugates

In order to determine the effect on solubility of covalent attachment of fatty acids of various chain length to SP-C, the following procedure was employed. One milligram of the various FA-SP-C conjugates was weighed out in preweighed microfuge tubes and dissolved in exactly 1 ml of methanol at 25° C. Thereafter, the suspension was bath sonicated for 30 seconds. The sample was then stored at 25° C. for fifteen minutes. The samples were then centrifuged at 4,500 g for 10 minutes after which time the supernatant was carefully removed. The remaining sample was then incubated at 37° C. for at least 16 hours in order to remove any remaining methanol. Thereafter, the microfuge tubes were again weighed and incubated for additional 2 hours at 37° C. Incubation was continued until a stable "dry weight" of the microfuge tubes was attained. By difference measurements the weight of the undissolved FA-SP-C conjugate (i.e. material which was not dissolved and hence removed upon supernatant withdrawal following centrifugation as described above) was determined.

The varying degrees of solubility are shown in Table 1. The extent of solubility is expressed as a relative percentage of recovered peptide.

TABLE 1

Relative Solubility of Fatty Acid-Sp-C Conjugates

| Fatty Acid Nomenclature | Fatty Acid Carbon Chain Length | Solubility * % |
|---|---|---|
| Unmodified | — | 17.1 |
| Acetic | C2 | 8.2 |
| Lauric | C12 | 23.9 |
| Myristic | C14 | 82.4 |
| Palmitic | C16 | 75.5 |
| Arachidic | C20 | 60.1 |

* Solubility was determined as described above.

It is clear from this data that covalent attachment of fatty acids of a carbon chain length greater than two (2) carbon atoms results in a marked improvement in solubility of the FA-SP-C conjugate as compared to unmodified SP-C. It is obvious from the data contained in Table 1 that the C-14

(myristic) and C-16 (palmitic) fatty acid conjugation to SP-C results in the most soluble material.

Tests were conducted to determine the biophysical (surface) activity of admixtures of synthetic phospholipids combined in vitro with each of the purified FA-SP-C conjugates either alone or in various combinations with full length SP-B(1–78) or a fragment thereof, SP-B(53–78).

EXAMPLE 3

Admixture Formulation

Prior to testing for surface activity, the modified and unmodified SP-C were admixed with lipids. A lipid mixture consisting of 67% 1,2 dipalmitoyl-sn-phosphatidylcholine (DPPC), 22% egg phosphatidylglycerol (PG) and 9% palmitic acid on a weight basis was prepared by dissolving the lipids in chloroform:methanol (2:1). The required amount of peptide (2%) was dissolved in methanol and heated to 60° C. for 10 minutes and then cooled to 45° C. and gently sonicated for 30 seconds in a bath sonicator. The peptide solution was then added to the lipid mixture prewarmed to 45° C. Samples were mixed at 45° C. by gentle swirling on a Buchi rotavap. The organic solvents were then evaporated at 45° C. through the application of a vacuum (600 torr). Following evaporation, the solids were then suspended in 10% ethanol in deionized distilled water with gentle bath sonication for 30 seconds. The sonicated suspension was then gently mixed for 30 minutes at 45° C. Thereafter, the ethanol was removed through the application of a vacuum (150 torr). Following complete removal of ethanol the suspension was diluted with 0.15M NaCl to yield an admixture with a phospholipid concentration of 25 mg/ml. Following formulation the admixtures were stored at 4° C. for 48 hours prior to testing.

The fatty acid modified peptides were either mixed with the lipids only, or with a full length SP-B peptide (SP-B (1–78)) or with the C-terminal SP-B fragment (SP-B (53–78)) plus lipids. The synthetic SP-B [SP-B(1–78) or SP-B(53–78)] fragments were prepared in a manner analogous to that described in Example 1 but the amino acid sequence was based on that of natural SP-B.

The peptide/lipid admixtures were formed at final peptide concentrations of 0.5 mg/ml (equivalent to 2% of solids concentration). When more than one peptide was employed in the admixture, the total final peptide concentration was always maintained at 0.5 mg/ml (2% of solids). If two peptides were used then each was used at a final concentration of 0.25 mg/ml.

In order to determine relative surface activity of these admixtures, they were compared to commercially available natural surfactants (Surfactant TA, Abbott Laboratories; Surfacten, Tokyo Tanabe), commercially available synthetic surfactants, (Exosurf, Burroughs-Welcome), and an admixture containing unmodified SP-C and a synthetic lipid only admixture standard. The commercially available surfactants were utilized as received. Biophysical activity was assayed using both the modified Wilhelmy balance (Langmuir Trough) system and the pulsating bubble surfactometer (PBS). For clarity these techniques are briefly described below.

EXAMPLE 4

Modified Wilhelmy Surface Balance (a) Surface tension versus compressed surface area.

The dynamic surface tension lowering properties of the peptide/lipid admixtures were studied using a modified Wilhelmy Surface Balance (Langmuir Trough). The instrument consists of an all Teflon trough and movable Teflon ribbon (dam) barrier system which completely contains and defines a variable surface area. Surface area was varied through the use of a constant rate reversible 3-phase motor to drive the Teflon barrier. A Cahn 2000 electrobalance (Cahn Instruments, Cerittos, Calif.) with a sandblasted 1 cm platinum plate and stainless steel hangdown wire was employed to determine the surface tension at the liquid-air interface. The entire apparatus was situated in a thermostated incubator set at 45° C. Surface area-surface tension measurements were made by adding 950 ml of 0.15 M NaCl to the trough. Subphase temperature was controlled during the measurements at 36–38° C.

For each experiment 27 ul of peptide/lipid admixture was applied in a random array of 13 (≅2 ul) droplets to the surface of the temperature controlled subphase and allowed to spread spontaneously for 3 minutes. (The 27 ul application corresponds to 675 ug of phospholipid). The trough surface area was then cycled from a maximum (445 sq. cm) to a minimum (178 sq. cm) surface area and back to maximum at a cycling rate of 3 cycles/min (compression ratio 2.5:1). The dynamic surface tension vs surface area was recorded for 7 complete compression-expansion cycles for each application.

(b) Absorption Rate.

A procedure similar to that described by Notter, et al., *Pediatric Res.* 16, 515–519, (1982) was employed to determine the absorption rate in the absence of diffusion resistance. The modified Wilhelmy surface balance as described above was used. However, instead of using a Langmuir trough a round Teflon dish (5.1 cm diameter) was employed. The subphase, 70 ml of 0.15 M NaCl, was allowed to equilibrate to 37° C. in the incubator and was continuously stirred with a Teflon coated magnetic stirer. An aliquot of the peptide/lipid admixture containing 5 mg of total phospholipid was dispersed in 10 ml of 0.15 M NaCl by vortexing for 10 seconds. This dispersion was then added to the saline subphase. Surface tension lowering was monitored using a strip chart recorder connected to the electrobalance output and data collected for 20 minutes.

Details of these techniques are as described in Notter, et al., Pediatric Res. 16, 515–519, 1982; Notter et al., Chem Phys. Lipids 33, 67–80, (1983); Egan et al., J. Applied Physiol. 55, 875–883, (1983); Bermel et al., Lung 162, 99–113, (1984); Notter, et al., Pediatric Res. 20, 569–577, (1985); Holm, et al., Chem Phys Lipids 38, 287–298, (1985).

EXAMPLE 5

The Pulsating Bubble Surfactometer (PBS)

The PBS equipment (Electronetics, Buffalo, N.Y.) used was essentially equivalent to that described in detail by G. Enhorning, J. Appid. Physiol. 43, 198–203, (1977). Recordings were made of the pressure gradient across the wall of a small air bubble, communicating with ambient air by means of a narrow chimney stack, but otherwise entirely surrounded by a 40 ul volume of the peptide/lipid admixture. The admixture concentration employed for these studies was 1 mg/ml total phospholipid (0.02 mg/ml total peptide) and the diluent was 0.15 M NaCl. Immediately prior to loading the sample chamber, the diluted samples were sonicated for 15 seconds to remove any gas nuclei.

The pressure drop across the air-water interface was measured during pulsation by a pressure transducer, and the corresponding surface tension determined through the application of Young's law and the Laplace equation. Measurements were all made at 37° C. and the bubble pulsed at 20 cycles/minute to render respectively a maximum (1.1. mm) and a minimum (0.8 mm) bubble diameter. (This compression/expansion corresponds to a 50% change in the surface area of the air-water interface).

Dynamic surface tension and absorption are summarized in Tables 2 and 3 below. Table 2 summarizes the dynamic surface tension and adsorption data obtained with the various peptide-lipid admixtures on the Wilhelmy Balance-Langmuir Trough System and King-Clements Adsorption System, respectively. Table 3 summarizes the maximum and minimum surface tensions obtained with the pulsating bubble apparatus. To one skilled in the art, it is obvious that low minimum dynamic surface tension values and reduced adsorption surface tension values are desirable properties of a good surfactant formulation.

TABLE 2

Dynamic Surface Tension and Adsorption Values as determined by the Wilhelmy-Langmuir Trough and King-Clements Systems, respectively.

| Sample | Wilhelmy-Langmuir Trough (dynes/cm) | | | King-Clements[a] (dynes/cm) |
|---|---|---|---|---|
| | Min[b] | Max[b] | Equilibrum[c] | Adsorption |
| 1. Controls | | | | |
| Surfactant TA | 8.0 | 39.0 | 34.0 | 31.0 |
| Exosurf | 11.2 | 64.7 | 57.3 | 41.8 |
| Lipids only[d] | 20.5 | 69.0 | 69.2 | 62.0 |
| 2. One Peptide[e] | | | | |
| Unmodified SPC | 0.5 | 42.0 | 28.5 | 57.5 |
| $C_2$-SPC (1-34) | 8.5 | 64.0 | 56.5 | 62.3 |
| $C_{12}$-SPC (1-34) | 1.5 | 62.3 | 45.4 | 52.8 |
| $C_{14}$-SPC (1-34) | 0.3 | 52.7 | 28.8 | 37.8 |
| $C_{16}$-SPC (1-34) | 3.4 | 61.7 | 38.1 | 43.1 |
| $C_{20}$-SPC (1-34) | 0.0 | 57.0 | 28.2 | 60.9 |
| SPB (1-78) | 0.0 | 45.0 | 38.0 | 30.0 |
| SPB (53-78) | 0.1 | 49.3 | 40.0 | 45.0 |
| 3. Two Peptides[f] | | | | |
| Unmodified SPC + SPB (1-78) | 0.0 | 45.0 | 35.5 | 40.0 |
| $C_2$-SPC + SPB (1-78) | 0.0 | 45.0 | 36.0 | 30.0 |
| $C_{12}$-SPC + SPB (1-78) | 0.0 | 44.7 | 29.5 | 32.3 |
| $C_{14}$-SPC + SPB (1-78) | 0.2 | 41.7 | 25.5 | 29.9 |
| $C_{16}$-SPC + SPB (1-78) | 0.0 | 39.0 | 23.3 | 24.0 |
| $C_{20}$-SPC + SPB (1-78) | 0.0 | 36.8 | 28.0 | 26.0 |
| Unmodified SPC + SPB (53-78) | 0.3 | 41.5 | 37.8 | 35.4 |
| $C_2$SPC + SPB (53-78) | 0.0 | 51.5 | 42.8 | 44.2 |
| $C_{12}$SPC + SPB (53-78) | 0.2 | 46.5 | 41.3 | 35.9 |
| $C_{14}$SPC + SPB (53-78) | 0.0 | 39.0 | 24.8 | 24.1 |
| $C_{16}$SPC + SPB (53-78) | 0.0 | 39.9 | 25.7 | 24.0 |
| $C_{20}$SPC + SPB (53-78) | 0.2 | 40.0 | 24.5 | 24.1 |

[a]10 ml. of diluted sample (1:50) is added under constant agitation to 70 ml. of saline in the subphase. Temperature: 37° C.
[b]Minimum/Maximum values recorded during seven complete compression - expansion cycles. In all cases 675 μg of phopholipid was added to the Langmuir Trough at maximum dimensions of 445 sq. cm. Temperature: 37° C. Values reported are the average of 3 runs with samples ages of at least 24 hours.
[c]Equilibrium adsorption value reported after a three (3) minute spreading time. Temperature: 37° C. Values are the average of samples described above. Values reported are from 10 minutes.
[d]Tanaka Lipids: Diphosphatidyl choline:egg phosphoglyerol:palmitic acid: :67:22:9.
[e]Peptide concentration is 0.5 mg/ml (i.e. 2% of phospholipids).
[f]Total peptide concentration is 0.5 mg/ml; each peptide concentration is 0.25 mg/ml.

From the data contained in Table 2 above, it is clear that each of the synthetic FA-SP-C admixtures either alone or in combination with a SP-B fragment significantly reduces the minimum dynamic surface tension to an extent that is comparable or better than that exhibited by natural surfactant (e.g. Surfactant-TA). With one exception only, all of the Two Peptide Admixtures (cf. section 3 of Table 2) yield a dynamic surface tension value of less than 1 dyne/cm whereas natural surfactant (e.g. Surfactant-TA) yields a minimum dynamic surface tension of about 8 dynes/cm.

Table 3 summarizes the minimum and maximum surface tension values at the air-aqueous interface obtained for the various peptide-admixtures on the pulsating bubble surfactometer. As with the Wilhelmy Balance, to one skilled in the art it will be obvious that low surface tension values are a desirable property of a good surfactant admixture.

TABLE 3

Maxmimum and Minimum Surface Tension Values of Admixtures as Determined by the Pulsating Bubble Apparatus.

| Sample | Surface Tension Values (dynes/cm) | |
|---|---|---|
| | Minimum | Maximum |
| a. Controls | | |
| Survanta (lot #15-099-AR) | 5.5 | 38.0 |
| Lipid only | 17.0 | 65.0 |
| Exosurf | 29.0 | 60.0 |
| b. One Peptide (a) | | |
| Unmodified SPC (1-34) | 23.7 | 67.3 |
| $C_2$SPC (1-34) | 18.8 | 66.2 |
| $C_{12}$SPC (1-34) | 30.8 | 66.5 |
| $C_{14}$SPC (1-34) | 11.1 | 64.4 |
| $C_{16}$SPC (1-34) | 19.0 | 64.3 |
| $C_{20}$SPC (1-34 | 22.9 | 65.4 |
| SPB (1-78) | 4.2 | 49.0 |
| SPB (53-78) | 4.9 | 55.5 |
| c. Two Peptides (b) | | |
| Unmodified SPC (1-34) + SPB (1-78) | — | — |
| $C_2$SPC (1-34) + SPB (1-78) | 1.3 | 48.3 |
| $C_{12}$SPC (1-34) + SPB (1-78) | 2.4 | 48.3 |
| $C_{14}$SPC (1-34) + SPB (1-78) | 0.86 | 40.5 |
| $C_{16}$SPC (1-34) + SPB (1-78) | 0.62 | 40.6 |
| $C_{20}$SPC (1-34) + SPB (1-78) | 0.08 | 38.9 |
| Unmodified SPC (1-34) + SPB (53-73) | 0.5 | 47.6 |
| $C_2$SPC (1-34) + SPB (53-78) | 17.0 | 62.9 |
| $C_{12}$SPC (1-34) + SPB (53-78) | 2.8 | 48.3 |
| $C_{14}$SPC (1-34) + SPB (53-78) | 0.53 | 39.0 |
| $C_{16}$SPC (1-34) + SPB (53-78) | 0.62 | 34.7 |
| $C_{20}$SPC (1-34) + SPB (53-78) | 3.0 | 45.0 |

Data reported are the mean of triplicate values determined after 100 cycles, i.e. 5 minutes at a pulsation rate of 20 cycles/per minute.
All samples are run at a phospholipid concentration of 1 mg/ml and a temperature of 37° C. Diluent is 0.15$\underline{M}$ NaCl.

It is clear from the data contained in Tables 2 and 3 that the FA-SP-C conjugates according to this invention, produce markedly enhanced surface activity as compared to synthetic lipids alone or synthetic lipids plus unmodified SP-C.

The unusual surface activity exhibited by the admixtures containing myristic (C-14) and palmitic (C-16)-SP-C conjugates is both surprising and unexpected.

Industrial Applicability

This invention overcomes numerous problems associated with natural, synthetic or recombinant SP-C. It is quite apparent that production of a fatty acid modified SP-C results is increased solubility, ease of formulation and will thus enhance and accelerate the commercial production of pulmonary surfactant products.

The foregoing detailed description is given for clearness of understanding only, and no unnecessary limitation should be understood therefrom, as modifications will be obvious to those skilled in the art.

What is claimed is:

1. A purified composition of matter consisting of a covalently linked compound in physical admixture with at least one lipid, wherein said covalently linked compound consists of two parts and has the structural formula:

FA-SPC, wherein -SP-C is protein selected from the group comprising human, porcine, canine and bovine surfactant associated protein C (SP-C) produced by chemical or enzymatic synthesis or recombinant DNA means, wherein said SP-C protein comprises a sequence of thirty-four (34) amino acids, said sequence containing eleven (11) valine amino acid residues, nine (9) of said valine residues being contained in two (2) adjacent polyvaline stretches, said polyvaline stretches having a first stretch of six adjacent valine amino acid residues and a second stretch of three adjacent valine amino acid residues separated from the first stretch by two hydrophobic amino acid residues, said SP-C protein enhances surfactant-like activity of phospholipids in lungs of an animal, and is substantially resistant to protease, endoglycosidase F and collagenase enzymes, and wherein FA- is a single fatty acid selected from the group comprising fatty acids having a carbon chain length from two(2) to about twenty(20) carbon atoms and wherein said fatty acid is covalently attached to the amino end terminal amino acid residue of said SP-C.

2. A composition of matter according to claim 1 wherein said SP-C is selected from the group of peptides having the amino acid sequence comprising:

$$\overset{1}{|}\phantom{X_{aa1}}\overset{5}{|}\phantom{Pro-Cys}\overset{10}{|}\phantom{Leu-Lys}\overset{15}{|}$$
$$X_{aa1}\text{-}X_{aa2}\text{-}Pro\text{-}Cys\text{-}Cys\text{-}Pro\text{-}Val\text{-}X_{aa3}\text{-}Leu\text{-}Lys\text{-}Arg\text{-}Leu\text{-}Leu\text{-}Ile\text{-}Val\text{-}Val\text{-}$$
$$\overset{20}{|}\phantom{Val-Val}\overset{25}{|}\phantom{Ile-Val}\overset{30}{|}\phantom{Gly-Ala}\overset{34}{|}$$
$$Val\text{-}Val\text{-}Val\text{-}Val\text{-}Leu\text{-}Ile\text{-}Val\text{-}Val\text{-}Val\text{-}Ile\text{-}Val\text{-}Gly\text{-}Ala\text{-}Leu\text{-}Leu\text{-}Met\text{-}Gly\text{-}Leu$$

wherein $X_{aa1}$ is selected from the group consisting of Leu, Gly, Arg, lle, and wherein $X_{aa2}$ is selected from the group consisting of Ile and Pro, and wherein $X_{aa3}$ is selected from the group consisting of His and Asn.

3. A composition of matter according to claim 1 wherein FA- is selected from the group of fatty acids having a carbon chain length of twelve(12) to sixteen (16) carbon atoms.

4. A composition of matter according to claim 3 wherein FA- is selected from the group of unsaturated or polyunsaturated fatty acids.

5. A composition of matter according to claim 1 wherein said FA- is selected from the group of fatty acids consisting of myristic, palmitic and arachidic acids.

6. A composition of matter according to claim 1 wherein said lipid is selected from the group consisting of synthetic phospholipids, naturally occurring phospholipids, neutral lipids, cholesterol, cholesterol esters, phosphatidyl choline, disaturated phosphatidylcholine, phosphatidyl glycerol, dipalmitoylphosphatidylcholine, phosphatidyl inositol and mixtures thereof.

7. A method for treating hyaline membrane disease or other syndromes associated with insufficient or abnormal surfactant material said method comprising administration of an effective amount of a surfactant composition to a patient in need of treatment, said surfactant composition consisting of at least FA-SPC and at least one lipid according to claim 1.

8. A method for treating hyaline membrane disease or other syndromes associated with insufficient or abnormal surfactant material said method comprising administration of an effective amount of a surfactant composition to a patient in need of treatment, said surfactant composition consisting of at least FA-SPC and at least one lipid according to claim 7 wherein said lipid is selected from the group consisting of synthetic phospholipids, naturally occurring phospholipids, neutral lipids, cholesterol, cholesterol esters, phosphatidyl choline, disaturated phosphatidylcholine, phosphatidyl glycerol, dipalmitoylphosphatidylcholine, phosphatidyl inositol and mixtures thereof.

9. A purified composition of matter consisting of a covalently linked compound in physical admixture with at least one lipid, wherein said covalently linked compound consists of two parts and has the structural formula: FA-SPC, wherein -SP-C is protein selected from the group comprising human, porcine, canine and bovine surfactant associated protein C (SP-C) produced by chemical or enzymatic synthesis or recombinant DNA means, wherein said SP-C protein comprises a sequence of thirty-four (34) amino acids, said sequence containing eleven (11) valine amino acid residues, nine (9) of said valine residues being contained in two (2) adjacent polyvaline stretches, said polyvaline stretches having a first stretch of six adjacent valine amino acid residues and a second stretch of three adjacent valine amino acid residues separated from the first stretch by two hydrophobic amino acid residues, said SP-C protein enhances surfactant-like activity of phospholipids in lungs of an animal, and is substantially resistant to protease, endoglycosidase F and collagenase enzymes, and wherein FA- is a single fatty acid selected from the group comprising fatty acids having a carbon chain length from two(2) to about twenty(20) carbon atoms and wherein said fatty acid is covalently attached to the carboxyl end terminal amino acid residue of said SP-C.

10. A composition of matter according to claim 9, wherein said SP-C is selected from the group of peptides having the amino acid sequence comprising:

$$\overset{1}{|}\phantom{X_{aa1}}\overset{5}{|}\phantom{Pro-Cys}\overset{10}{|}\phantom{Leu-Lys}\overset{15}{|}$$
$$X_{aa1}\text{-}X_{aa2}\text{-}Pro\text{-}Cys\text{-}Cys\text{-}Pro\text{-}Val\text{-}X_{aa3}\text{-}Leu\text{-}Lys\text{-}Arg\text{-}Leu\text{-}Leu\text{-}Ile\text{-}Val\text{-}Val\text{-}$$
$$\overset{20}{|}\phantom{Val-Val}\overset{25}{|}\phantom{Ile-Val}\overset{30}{|}\phantom{Gly-Ala}\overset{34}{|}$$
$$Val\text{-}Val\text{-}Val\text{-}Val\text{-}Leu\text{-}Ile\text{-}Val\text{-}Val\text{-}Val\text{-}Ile\text{-}Val\text{-}Gly\text{-}Ala\text{-}Leu\text{-}Leu\text{-}Met\text{-}Gly\text{-}Leu$$

wherein $X_{aa1}$ is selected from the group consisting of Leu, Gly, Arg, lle, and wherein $X_{aa2}$ is selected from the group consisting of Ile and Pro, and wherein $X_{aa3}$ is selected from the group consisting of His and Asn.

11. A composition of matter according to claim 9 wherein FA- is selected from the group of fatty acids having a carbon chain length of twelve(12) to sixteen (16) carbon atoms.

12. A composition of matter according to claim 11 wherein FA- is selected from the group of unsaturated or polyunsaturated fatty acids.

13. A composition of matter according to claim 9 wherein said FA- is selected from the group of fatty acids consisting of myristic, palmitic and arachidic acids.

14. A composition of matter according to claim 9 wherein said lipid is selected from the group consisting of synthetic phospholipids, naturally occurring phospholipids, neutral lipids, cholesterol, cholesterol esters, phosphatidyl choline, disaturated phosphatidylcholine, phosphatidyl glycerol, dipalmitoylphosphatidylcholine, phosphatidyl inositol and mixtures thereof.

15. A method for treating hyaline membrane disease or other syndromes associated with insufficient or abnormal surfactant material said method comprising administration of an effective amount of a surfactant composition to a patient in need of treatment, said surfactant composition consisting of at least FA-SPC and at least one lipid according to claim 9.

16. A method for treating hyaline membrane disease or other syndromes associated with insufficient or abnormal surfactant material said method comprising administration of an effective amount of a surfactant composition to a patient in need of treatment, said surfactant composition consisting of at least FA-SPC and at least one lipid according to claim 15 wherein said lipid is selected from the group consisting of synthetic phospholipids, naturally occurring phospholipids, neutral lipids, cholesterol, cholesterol esters, phosphatidyl choline, disaturated phosphatidylcholine, phosphatidyl glycerol, dipalmitoylphosphatidylcholine, phosphatidyl inositol and mixtures thereof.

* * * * *